United States Patent [19]

Armstrong

[11] 4,066,183

[45] Jan. 3, 1978

[54] CHROMATOGRAPHIC SEPTUM HAVING POLYIMIDE COATING

[75] Inventor: Nelson W. Armstrong, Hoffman Estates, Ill.

[73] Assignee: L. C. Company, Inc., Schaumburg, Ill.

[21] Appl. No.: 771,689

[22] Filed: Feb. 24, 1977

[51] Int. Cl.² .................. B32B 3/02; B32B 27/06; B32B 27/28; B65D 59/02
[52] U.S. Cl. .................. 215/247; 128/DIG. 14; 215/DIG. 2; 215/DIG. 3; 215/DIG. 4; 427/407 C; 428/64; 428/422; 428/474
[58] Field of Search ............ 428/421, 422, 474, 64; 128/DIG. 14; 215/DIG. 2, DIG. 3, DIG. 4, 247; 427/407

[56] References Cited

U.S. PATENT DOCUMENTS

| | | | |
|---|---|---|---|
| Re. 24,856 | 8/1960 | Panagrossi et al. | 428/421 |
| 2,747,756 | 5/1956 | Hartop et al. | 215/427 |
| 2,809,130 | 10/1957 | Rappaport | 428/422 |
| 2,945,773 | 7/1960 | Panagrossi et al. | 428/422 |
| 2,947,325 | 8/1960 | McFarland | 428/422 |
| 3,205,113 | 9/1965 | McFarland | 428/422 |
| 3,463,339 | 8/1969 | McGuckin | 215/247 |
| 3,484,337 | 12/1969 | Starita | 215/DIG. 3 |
| 3,551,273 | 12/1970 | McKinney | 215/247 |
| 3,552,591 | 1/1971 | Wimmer | 128/DIG. 14 |
| 3,579,370 | 5/1971 | Punderson et al. | 428/422 |
| 3,684,646 | 8/1972 | Kruez | 428/421 |
| 3,760,969 | 9/1973 | Shimamoto et al. | 215/DIG. 3 |
| 3,770,566 | 11/1973 | Gerow | 428/421 |
| 3,791,909 | 2/1974 | McKee | 428/421 |
| 3,898,363 | 8/1975 | Ward et al. | 428/474 |

*Primary Examiner*—J.C. Cannon
*Attorney, Agent, or Firm*—Darbo & Vandenburgh

[57] ABSTRACT

Improved septa for chromatographic apparatus and procedures comprise disc or cylindrical bodies of silicone rubber with a coating of polyimide which may in turn be covered by a coating of Teflon.

4 Claims, 3 Drawing Figures

CHROMATOGRAPHIC SEPTUM HAVING POLYIMIDE COATING

BACKGROUND AND SUMMARY OF THE INVENTION

In chromatographic apparatus and procedures, closures for containers, columns and the like are commonly in the form of appropriately shaped bodies of silicone rubber or similar material which can be penetrated by a hypodermic needle for access to the contents of the container with immediate healing of the hole pierced in the body by the needle when the needle is withdrawn to maintain the sealing closure. The escape of any part of the contents of the container and access of the atmosphere are both prevented by the use of such septa.

While very convenient, the use of such septa is not without some problems. A major problem results from the bleeding from the silicone rubber due to the action of the material confined in the container or chromatographic system, resulting in contamination of the material. The problems are aggravated at higher temperatures. Attempts to isolate the silicone rubber from access by the contents of the containers have been partially successful in mitigating the contamination problem. The approach has been to provide a barrier coating, most commonly tetrafluoroethylene, upon at least the surface of the septum body which is to be exposed to the interior of the container or chromatographic system. Teflon offers only limited stability at high temperatures and contains fluorine, a halogen, which in even trace quantities greatly interferes with radio-active detectors, such as the highly sensitive electron capture detectors used for trace pesticide or organic halide analyses.

The object of this invention is to provide chromatographic septa which may be safely employed to close containers, columns, and the like, especially in chromatographic apparatus, which are provided with barrier coating that is inert to substantially all known organic solvents and is stable to about 400° C. Septa bleed is effectively minimized and the barrier coating does not affect electron capture detectors.

This object is attained by providing silicone rubber septa having a coating of polyimide polymer applied directly upon and securely bonded to the surface of the septa. If desired for certain applications, the polyimide coating may itself be coated with Teflon to enhance resistance of the barrier coating to moisture.

BRIEF DESCRIPTION OF THE DRAWING

In the accompanying drawing.

DESCRIPTION OF SPECIFIC EMBODIMENTS

Figure 1:
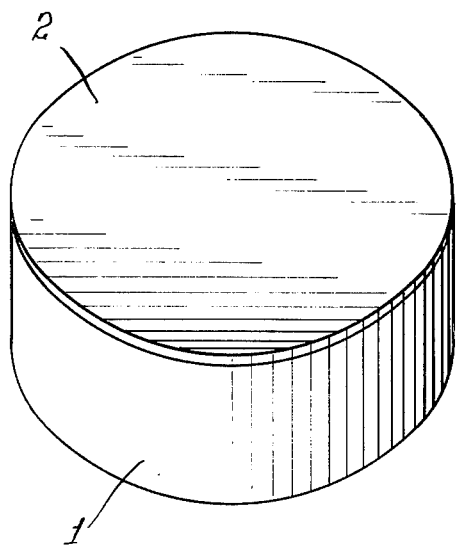
FIG. 1 is a perspective view of a disc septum having a polymide coating on one flat surface.

Three examples of chromatographic septa embodying the invention are shown in the drawing. Referring to FIG. 1, the body 1 of the disc-shaped septum may be formed from a suitable organic silicone gum rubber, a suitable fluoro elastomer, such as that supplied by E. I. du Pont Co. under the trademark "Viton", or other rubber having the necessary characteristics. One flat surface is covered by a coating 2 of the polyimide polymer produced by a poly-condensation reaction between an aromatic tetrabasic acid and an aromatic amine, the particular material found to be suitable being that supplied by E. I. du Pont Co. under the trademark "Kapton". Another suitable polyimide is the material currently supplied under the trademark "Kymid".

This polyimide polymer is very inert chemically and has no known organic solvent. It exhibits a very high temperature stability, dependably resisting temperatures up to 400° C. while polytetrafluoroethylene polymers tend to soften or decompose at temperatures of about 250° C. The polyimide surface is exposed to the material in a container or interior of a closed chromatographic system and prevents contact of the material with the rubber which forms the body of the septum. While the thickness of the coating is not critical, it has been found that a coating approximately one mil thick is satisfactory.

Figure 2:
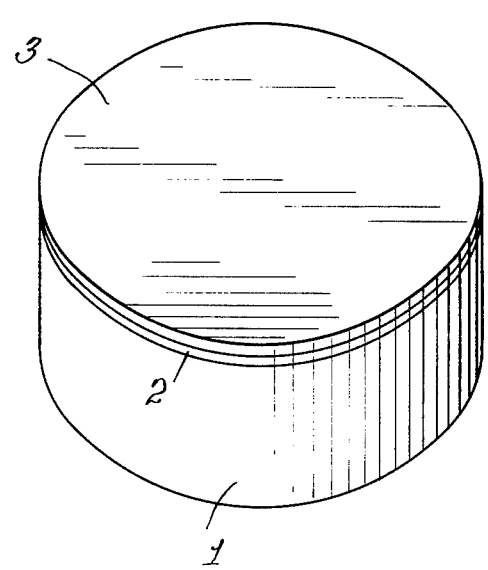
FIG. 2 is a perspective view of a disc septum similar to that of FIG. 1 but having a coating of Teflon over the polymide barrier.

The disc septum illustrated in FIG. 2 is similar to that described with reference to FIG. 1 having a body 1 covered on one flat surface with a film 2 of polyimide polymer, but is provided with an additional coating 3 of Teflon. The Teflon, which adheres strongly to the polyimide film, enhances the moisture resistance of the polyimide film. The composite barrier provides complete isolation of the silicone rubber body of the septum to the material within the container or chromatographic system.

Figure 3:
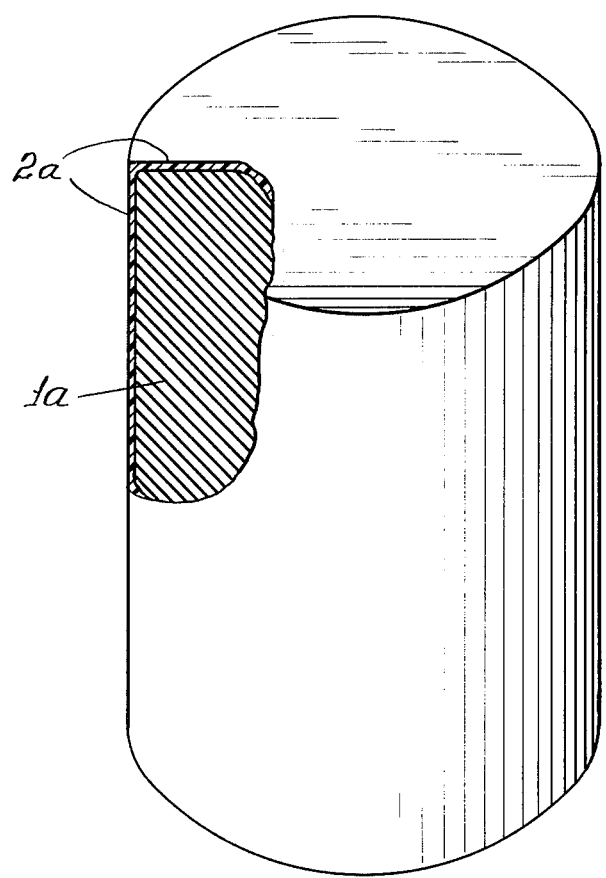
FIG. 3 is a perspective view, partly in section, showing a cylindrical septum coated on the sides as well as one end by the polymide barrier.

A cylinder septum is illustrated in FIG. 3. The body 1a of silicone rubber or other suitable material is coated not only over an end surface but also on the cylindrical sides, this coating of polyimide polymer 2a ensuring isolation of the rubber septum material from the material in the container or chromatographic system.

It will be understood from the foregoing that the improved chromatographic septa of this invention provides the convenience of a closure which can be penetrated by the hypodermic needle of a syringe with self-healing of the pierced opening following withdrawal of the needle while at the same time providing a closure which dependably seals the container or system with which it is used without adversely affecting in any way the use or accuracy of the chromatographic apparatus. Of particular importance, the polyimide polymer contains no halide so that the halide contamination which is inadmissable for certain analytical procedures is entirely avoided.

I claim:

1. In a chromatographic septum comprising a body of hypodermic needle penetrable self-healing rubber adapted to serve as a closure for a container or chromatographic system, the improvement which comprises covering the surface of the septum that is to be exposed to the interior of the container or system with a coating of polyimide polymer.

2. The septum of claim 1 wherein the septum is disc-shaped and at least one flat surface thereof is coated with the polyimide polymer.

3. The septum of claim 1 wherein the coating is itself covered by a coating of tetrafluoroethylene.

4. The septum of claim 1 wherein the septum is cylinder-shaped and the cylindrical sides as well as at least one end of the septum body is coated by the polyimide polymer.

* * * * *